United States Patent [19]

Gancy

[11] Patent Number: 4,699,725

[45] Date of Patent: Oct. 13, 1987

[54] MAGNESIUM CALCIUM ACETATE PRODUCTS, AND PROCESS FOR THEIR MANUFACTURE

[76] Inventor: Alan B. Gancy, 265 Robineau Rd., Syracuse, N.Y. 13209

[21] Appl. No.: 941,171

[22] Filed: Dec. 12, 1986

[51] Int. Cl.$^4$ .............................................. C09K 3/18
[52] U.S. Cl. ...................................... 252/70; 106/13; 562/607; 562/608
[58] Field of Search ........................... 252/70; 106/13; 562/607, 608

[56] References Cited

U.S. PATENT DOCUMENTS 4,488,978 12/1984 Gancy .................................. 252/70
4,606,836 8/1986 Gancy .................................. 252/70

*Primary Examiner*—Robert A. Wax

[57] ABSTRACT

Finely divided ore blends containing chemically active magnesium oxide and calcium oxide are physically combined with a critical amount of water prior to reaction with acetic acid. Intermediate products range in physical consistency from putty-like masses to viscous liquors, depending upon the relative fraction of magnesium oxide in the ore feed. Intermediate products freeze to form hydrates of magnesium calcium acetate, the freeze times being dependent upon a number of chemical and physical parameters. Product drying requirements range from minimal drying to none at all, depending upon the magnesium fraction in the products. Products are non-friable and have excellent crush strength, and are suitable for storage, shipping and application in chemical deicing as well as other end use applications where crude low-cost materials are called for.

A unique situation centers around the composition corresponding to the magnesium mol fraction of 0.8. This material requires no drying and exhibits an extraordinary high crush strength. Additionally, as much as 75% by weight of traction agent (sand) can be successfully incorporated into this material without the aid of chemical binders.

12 Claims, No Drawings

4,699,725

MAGNESIUM CALCIUM ACETATE PRODUCTS, AND PROCESS FOR THEIR MANUFACTURE

BACKGROUND OF THE INVENTION

Calcium magnesium acetate has emerged in recent years as a viable non-polluting replacement for salt, or sodium chloride, as a surface deicer. Research and development by the states as well as the Federal government has focussed on compositions of lower magnesium content, in spite of the anticipation that higher magnesium content materials hold promise as superior deicers. The blockage has been in the technology of manufacture. The present invention clears that blockage, and results in process innovations as well as new compositions known as magnesium calcium acetates.

DESCRIPTION OF PRIOR ART

In U.S. Pat. No. 4,606,836, I describe a commercially successful process for the manufacture of calcium magnesium acetate deicer. The magnesium content of the products in that case covered the mol fraction range 0.5–0.67, where magnesium mol fraction is defined as follows:

$$X_{Mg} = \frac{\text{mols Mg}}{\text{mols Mg} + \text{mols Ca}}.$$

The major reason for limiting $X_{Mg}$ to 0.67 centered around the problem of incomplete chemical reaction of the magnesium-based raw material. As $X_{Mg}$ increased, the magnesium-based raw material, usually magnesium oxide, or MgO, would tend to become encapsulated in product calcium magnesium acetate. More specifically, it was the hydrated magnesium acetate component of the product mass which comprised a highly viscous, glassy material which seriously inhibited good contact between free (acetic) acid and MgO raw materials.

It was clear in that case that the calcium-based raw material component, usually calcium oxide, or CaO, reacted more energetically with raw material acetic acid. Thus the CaO component would react preferentially with the acid, and the MgO component reacted in a later stage. Additionally, the CaO reaction resulted in a large exotherm; this heat in turn helped to drive the reaction between MgO and acid.

Thus as the value of $X_{Mg}$ increased in the attempted syntheses, two events occurred in concert to inhibit thorough reaction of the MgO component:
1. raw material encapsulation increased
2. the size of the exotherm decreased The undesirable consequence of incomplete utilization of MgO raw material is twofold. Firstly, the unreacted ore gives rise to undesirable insoluble matter when the deicer becomes dissolved in water during use. This would become a minor problem in areas where sewer systems receive the surface waters; these are the same areas where sand or other traction agents are proscribed because of potential plugging of sewer systems. Secondly and more important, unreacted raw material acetic acid can become entrapped in the product which in turn produces an acid reaction in end use. It has been shown that a 10% calcium magnesium acetate solution in water must have a pH of at least 8 if it is not going to attack certain metals, or Portland cement concrete.

The mechanism of acid entrapment is the formation of the known compound magnesium acid-acetate, and/or calcium acid-acetate.

Even the phenomenon of acid entrapment can be handled, and that is by heating the product. Heat decomposes the acid-acetate(s) and drives off free acetic acid, in addition to water. But product drying adds roughly 15% to the capital cost of the production plant, and roughly 5% up to the operating cost. Thus product drying is preferably avoided, and indeed is one of the key features of the instant invention.

The expedient of inputting less tha the stoichiometric requirement of acetic acid, so as to avoid an acidic product, has been attempted. This approach has been rejected, however, as it only leads to an escalation of the problem of residual insoluble MgO in the product. It also results in a waste of raw material ore.

Thus, for all the reasons given, successful manufacturing operations involving products having an $X_{Mg}$ value greater than 0.67 had heretofore been frustrated. Yet there are compelling reasons for extending the $X_{Mg}$ value beyond 0.67, indeed all the way to 1.0 which corresponds to magnesium acetate. Where such products are to be used as deicers, these reasons are as follows:
1. The water-eutectics (freezing points) of solutions of these products in water are substantially reduced as $X_{Mg}$ moves from 0.67 to 1.0. In essence, this means that the materials become superior deicers.
2. The rate of dissolution in water of these products increases as $X_{Mg}$ moves from 0.67 to 1.0. This means that the deicers act more quickly when applied in an ice-melting situation.

There are other end-uses for magnesium calcium acetate products which could benefit through an increase in the value of $X_{Mg}$. For example, a crude low-cost magnesium acetate does not now exist on the market today, so that end uses are restricted to those which can support the cost of the refined magnesium acetate which is an article of commerce.

It is one object of the prior art to incorporate sand or other traction agent into the calcium magnesium acetate particles. Whereas this has been successful, as described in U.S. Pat. No. 4,606,836, there has been a limitation on the size of the particles which could in fact be produced. For example, a product containing 75% sand seems to be preferred by users. Yet it had been difficult to produce larger particles of this 75%-sand product using existing technology.

It is the object of the present invention to resolve all of the difficulties heretofore described.

OBJECTS OF THE INVENTION

One object of the invention is to provide an economical, industrially feasible process for the production of a relatively non-polluting magnesium calcium acetate deicer.

It is a further object to produce a low-cost magnesium acetate product suitable for use as a deicer, and for other end uses.

Yet another object is to produce a relatively non-friable magnesium calcium acetate product which can be successfully stored, shipped, and disppensed.

A further object of the invention is to provide a manufacturing process for making magnesium calcium acetate which requires a minimum of processing energy for process drying.

Another object is an embodiment of a magnesium calcium acetate manufacturing process which requires no drying step.

A further object of the invention is to provide a unique magnesium calcium acetate composition of matter which epitomizes favorable processing as well as product characteristics.

Another object is to produce a superior line of magnesium calcium acetate products by reacting the appropriate ore-blend with acetic acid, which rection is characterized by the absence of recycle streams, waste products, co-products, or by-products.

Yet another object is to produce a series of magnesium calcium acetate products which resist degradation in high temperature, high humidity environment.

A further object of this invention is to provide superior, relatively non-polluting, and relatively non-corrosive deicers/anti-icers.

It is also an object of this invention the introduction of a coarse-particle magnesium calcium acetate product incorporating relatively high levels of sand or other traction agent.

A further object is to provide a relatively rapidly dissolving magnesium calcium acetate for commerce.

SUMMARY OF THE INVENTION

In general, mixtures or blends of finely divided dolomitic lime and magnesium oxide are treated with a critically controlled amount of water, the whole then reacted with glacial acetic acid. Mixtures of ores other than the ores named will be suitable to the process providing they provide the desired levels of chemically reactive MgO and CaO. Also, dilute acetic acid can be used, and reacted directly with the dry ore blend.

I have discovered that the amount of input water, as in the prior art, is critically important to the success of this low-cost processing scheme. But two very important departures have been discovered:
1. A greater amount of input water is required than had heretofore been practiced when operating at higher values of $X_{Mg}$, and
2. The amount of input water must be adjusted according to the mol fraction $X_{Mg}$ of magnesium desired in the product.

Thus there is not a single reaction formula, but a continuously varying one depending upon the $X_{Mg}$ value desired in the product, i.e., depending on the active MgO/CaO ratio in the ore blend selected.

Furthermore it has been discovered that ore utilization is enhanced whenever the ore is first comingled with the water required. Better results are obtained this way than if all required water were added to the glacial acetic acid, so as to form an acid solution reactant. Even at an $X_{Mg}$ value of 1.0, where the product is straight magnesium acetate, it can be shown that virtually all of the active MgO reactant is converted whenever 1. just sufficient water is introduced which leads to a solid product, and 2. that water is first added to the ore, blending well, prior to introduction of concentrated acetic acid.

Water introduced to the ore does not slake the MgO component, as this is known to take a matter of weeks at room temperature. Neither does it slake the CaO component as evidenced by the absence of exotherm. The CaO component doesn't slake for two reasons: insufficient time is allowed for slaking to initiate, and the presence of MgO functions as a diluent and heat absorber, thus inhibiting the CaO slaking process from taking off.

I have thus found that when five mols of water, including the water produced by the chemical reaction between ore and acid, are introduced per mol of input MgO, the reaction scheme is successful in producing a solid product. For example,

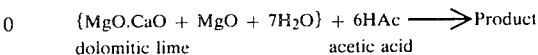
{MgO.CaO + MgO + 7H$_2$O} + 6HAc ⟶ Product
dolomitic lime      acetic acid In this case there are two mols of input MgO, requiring a total of ten mols input water. But 3 of these mols of water emanate from the acetic acid. Thus only 7 mols of liquid water are actually introduced.

The procedure is to blend the dolomitic lime and MgO thoroughly, then to mix this blend in turn with all the required water. This is why the ore and water are included in the same brackets. Wetted ore and glacial (in this case) acetic acid are then combined with agitation to form the product batch. Note that in this example the value of $X_{Mg}$ is 0.67. The product consists of 2 mols of (hydrated) magnesium acetate to every mol of calcium acetate.

At the value of $X_{Mg}$ in the example, the immediate product has a putty-like consistency which spontaneously freezes into a relatively hard material. The freezing is a chemical process whereby the molten magnesium acetate converts to a crystalline hydrate. Such material becomes even harder when allowed to stand and lose a small fraction of its water by air-drying. Industrially, air-drying is not feasible; a low temperature drying can be introduced which avoids melting of magnesium acetate tetrahydrate, i.e., operates well below 70° C.

When the value of $X_{Mg}$ approaches 1.0, the reaction batch increasingly goes through a viscous phase. Indeed, at $X_{Mg}=1$, no insolubles are present, and the batch is a near-transparent viscous liquid. These intermediate states also spontaneously freeze to form a solid product. In general, these products require a curing during which the solid particles become much harder, or they require a slight drying in order to become rock hard.

There is however, a unique occurrence at and near $X_{Mg}=0.80$ where the reaction batch goes through a viscous phase to produce a product which is extremely hard without curing or drying. This product contains 4 mols of hydrated magnesium acetate per mol of calcium acetate. It could double as traction agent and deicer/anti-icer.

Note that all of the input water does not end up in the product. This is due to the reaction exotherm, even at $X_{Mg}=1$. Thus, in the process of invention, 5 mols of water are introduced for every mol of magnesium acetate product formed. Some water is evolved in processing, such that something approximating 4 mols of water end up in the product relative to mols of magnesium acetate. In this case, $X_{Mg}=1$, it is very clear (Example I) that a lower water input level results in an incomplete utilization of MgO.

The amount of acetic acid introduced is generally the stoichiometric equivalent of the active CaO, MgO content of the ore blend. Under this condition, solution of the product in water (10%, anhydrous product basis) would approximate 7.2 in pH. If a lower or higher pH in the product solution is required, the ore/acid ratio can be slightly altered. For end use as a deicer, the preferred pH range is 8–9. in this case a slight excess of ore is required. The solution of such a product in water exhibits a turbidity due to excess base. It is suspected that such turbidity arises through the formation of relatively insoluble basic acetates.

The actual processing of intermediate stages of the product of this invention can proceed in a number of ways, depending upon the value of $X_{Mg}$. When $X_{Mg}$ equals unity, processing proceeds in exactly the same manner as in the production of aluminum sulfate worldwide. Here a viscous, hot product solution is poured onto a flat surface where it ultimately freezes. The frozen material is then mechanically broken up and fed to conventional crushers.

Alternatively, raw material ore, water and acid streams are simultaneously introduced to an agitated vessel containing an existing bed of crystalline product. Commercial disc or drum pelletizers are suitable for the purpose. A somewhat more flexible commercial unit is known as a horizontal pelletizer; in this case, raw material streams can be introduced at selected points along the horizontal flow of materials. The horizontal pelletizer is especially useful when it is required to introduce a traction agent such as sand into the magnesium calcium acetate product.

Individual cases may require modification of the basic equipment in order to manufacture under optimal conditions. For example, a so-called re-roll device is used following the drum pelletizer stage in order to prevent the product from growing beyond the specified particle size. The re-roll device permits continuation of the chemical reaction, including crystallization or freezing, without introducing additional raw material. It is thus a special way of increasing product residence time.

The time period for an intermediate stage to freeze depends upon a number of variables. It is therefore impossible to give specific numbers without at the same time specifying a number of other parameters.

The factors which influence freezing can be generally described as follows:
1. Peak Temperature of the Reaction Batch—In general, the higher the temperature allowed to be approached as a result of the reaction exotherm, the longer the batch will take to freeze.
2. Temperature of the Reaction Batch—With peak temperature specified, the longer the system is kept hot, the longer it will take to freeze.
3. Presence of Surface Active Agents—When lignosulfonates are used to help disperse the ore into the water, or used as binders, the intermediate stages require greater time to freeze.
4. Introduction of Foreign Materials—Introduction of dry sand to intermediate reaction stages has been found to promote freezing. Whether this is due to the (slight) thermal shock, or to a nucleation process is undetermined.
5. The Value of $X_{Mg}$—At $X_{Mg}=0.67$ the reaction intermediate took 57 minutes to freeze. Under similar conditions, a $X_{Mg}=1.0$ batch required 100 minutes. An intermediate $X_{Mg}$ product having a value of 0.8 started freezing at 47 minutes, and completed the freezing process at 72 minutes. In all cases, neither product crystals, sand, nor surface active agents were introduced. When dry sand is introduced, freezing times can be reduced to 1 or 2 minutes. When lignosulfonate is introduced, freezing times can be extended to more than 8 hours.

Thus, use of lignosulfonates or other surface active agents can ge used to control freezing, so desired. For example, in the industrial process requiring the pouring of viscous liquid onto a flat surface, surface active agents can be used to prevent premature freezing from spurious causes.

The incorporation of sand or other traction agent into magnesium calcium acetate products of this invention is very important when the products are to be used as deicers/anti-icers. In general, the more sand introduced as a fraction of the product the more difficult it is to produce a large (pea-size) product particle. At the 75% sand level, for example, the product at a lower level of $X_{Mg}$ tends to be smaller of particle size, and is actually little more than coated sand. At $X_{Mg}=1$ the product also tends towards a finer grained product because the cohesive forces within hydrated magnesium acetate are not great. These problems have been solved by the use of lignosulfonate binder.

However, an unanticipated result was discovered at $X_{Mg}=0.8$. Here the intermediate stage of reaction was plastic, and was mechanically transformed into large particles which froze within 22 minutes of acid introduction. No drying was required to yield a strong, non-friable product. No binder or dispersant was used. In this case, wet sand and ore were premixed, and acid was added to the whole.

DESCRIPTION OF PREFERRED EMBODIMENTS

The following examples will illustrate the embodiments of the invention:

EXAMPLE I

A. Illustrating Use of Insufficient Water Input. $X_{Mg}=1.00$

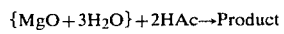
$$\{MgO+3H_2O\}+2HAc\rightarrow Product$$

300 parts MgO, 98% assay, were added to 394 parts of water, and the mixture thoroughly blended. To this blend were added 876 parts of glacial acetic acid, with stirring. A clear viscous liquor was formed which contained many small white specks. In 23 minutes the batch had cooled to room temperature, and there was no odor of acetic acid over the batch. In 122 minutes from the time of acid introduction, freezing autonomously occurs. There is a strong emanation of acetic acid odor at this point, signalling partial decomposition of the acid-acetate.

The frozen mass was mechanically broken into clumps. One day later there was still a strong acid odor over the batch.

B. Illustrating Use of Sufficient Water Input. $X_{Mg}=1.00$

$$\{MgO+4H_2O\}+2HAc\rightarrow Product$$

300 parts MgO were added to 536 parts water, and the mixture thoroughly blended. To this blend were added 876 parts of glacial acetic acid, with stirring. A clear viscous liquor was formed with no white particles visible. At 100 minutes from the time of acid introduction, the mass became crystalline accompanied by an exotherm. No odor of acid was evident. Product was broken into clumps which were semi-hard. Clumps were equilibrated with atmospheric air at about 52% relative humidity and 60° F., and were thus transformed into hard particles suitable for commerce.

Product composition is Mg(Ac)$_2$.3.91H$_2$O. The pH of a 10% solution is 7.2. There is virtually no solid residue, and a very minor amount of white flocculant solids.

EXAMPLE II

A. Illustrating Reaction Between Dry Ore Blend and Aqueous Acetic Acid $$X_{Mg}=0.67$$

300 parts of dolomitic lime, 96.7% assay, were thoroughly blended with 124 parts MgO, 98% assay. To this dry blend was added 1463 parts of homogeneous acetic acid solution prepared by blending 1084 parts of glacial acetic acid with 379 parts water. Reaction mixture was thoroughly agitated. A putty-like non-sticky solid product formed almost immediately.

At 96 minutes from the time of acid introduction, the product pellets were hard at exterior surfaces only. Seven hours subsequent to this, pellets were uniformly hard throughout.

The pH of a 10% solution of product (anhydrous basis) in water was 8.8. Product dissolved fairly rapidly to produce a solution containing a minor amount of sediment, and flocculant solids which eventually settled.

B. Illustrating Reaction Between Wetted Ore and Glacial Acetic Acid $$X_{Mg}=0.67$$

300 parts of dolomitic lime were blended with 124 parts MgO. To this blend were added 379 parts of water, and the system thoroughly blended. To the wet blend were added 1084 parts of glacial acetic acid, with agitation. A non-sticky, putty-like solid product formed almost immediately.

At 57 minutes from the time of acid introduction, the product froze to produce a uniformly hard consistency material. Product was broken into smaller chunks which were non-friable, and suitable for commerce.

The pH of a 10% solution of product was 8.8. Product solution was similar in appearance to that of IIA, excepting floc size was larger, and floc settled more slowly., Product composition is Ca(Ac)$_2$.2{Mg(Ac)$_2$.3.41H$_2$O}.

EXAMPLE III

Illustrating a Preferred Process/Product. $X_{Mg}=0.8$

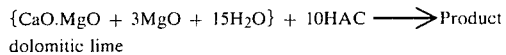
dolomitic lime

To a blend containing 200 parts dolomitic lime and 248 parts MgO were added 542 parts water, with agitation. To this wetted blend were added 1205 parts glacial acetic acid, with agitation. A viscous paste was formed which began to freeze 47 minutes after acid introduction. Freezing was complete in 72 minutes. No acetic acid odor was detected over the batch during or after crystallization. Product is rock hard, and can only be broken up using hammer and chisel.

pH of a 10% product solution in water is 8.4. Minor amount of sediment and settling turbidity present. 91 minutes after the sample froze the product weight was 91% of the input weight.

EXAMPLE IV

Illustrating a Preferred Process/Product $X_{Mg}=0.8$; 75% sand 200 parts dolime, 248 parts MgO, 542 parts water and 4434 parts of fine brick sand were thoroughly blended together. To this blend were added 1205 parts glacial acetic acid. A non-sticky workable plastic mass was formed almost immediately. Mass was mechanically converted to large semi-hard aggregates. No odor of acetic acid was detected emanating from this batch.

At 22 minutes after introduction of acid the product was hard. Elevated temperature drying was unnecessary. Product suitable for commerce without further treatment.

EXAMPLE V

Illustrating Relative Storage Stability of Hydrated Products of Invention $X_{Mg}=0.60$; % Sand = 75%

A. 330 parts of dolomitic lime, 70 parts MgO, 3723 parts of fine brick sand and 282 parts water were thoroughly blended. To this blend was added 1003 parts glacial acetic acid, with agitation. Then 213 parts water were gradually added until good pellets could be formed with agitation. A sample of this product was heated in a 110° C. oven for 90 minutes, whereupon it lost 10.4% in weight. The sample was cooled to room temperature and stored in an 84% relative humidity environment. Pellets were extremely hard. Seventeen and one-half hours later the sample pellets lost crush strength to the degree that they were no longer a viable article of commerce. Corresponding sample material which had not been oven-dried lost no strength under identical (side-by-side) storage conditions. Three days later the undried sample still retained its crush strength. At this point the experiment was terminated.

B. Example VA. experiment was repeated. Subsequent to the acid introduction step, however, an additional 50 parts water and 62 parts 58% Calcium Lignosulfonate solution in water ("Norlig A") were slowly added until good pellets could be formed. Sample was split, one portion remaining unheated. The other portion was heated to virtual constant weight in a 110° C. oven; weight loss was 8.7%. After 11 hours of storage at a relative humidity of 82% no difference between heated and unheated pellet crush strengths could be discerned. However, seven and one-half hours later the oven-dried sample dramatically lost crust strength. The unheated sample crush strength was undiminished.

Although this invention has been described in connection with specific forms thereof, it will be appreciated by those skilled in the art that a wide variety of equivalents may be substituted for those specific elements and steps of operation shown and described herein, that certain features may be used independently of other features, and that parts may be reversed, all without departing from the spirit and scope of this invention as defined in the appended claims.

I claim:

1. An economical process for the manufacture of magnesium calcium acetate hydrate comprising the following steps:
   a. introducing finely divided ore containing chemically active calcium oxide and chemically active magnesium oxide to an agitated reaction vessel such that the mol fraction of magnesium in said ore falls within the range 0.68–1.0;

b. introducing to said agitation reaction vessel a measured quantity of water such that the number of mols of water is numerically equal to x times the number of mols of said chemically active magnesium oxide, minus one-half the number of moles of acetic acid introduced where x equals 4.5–6;

c. introducing to said agitated reaction vessel a measured amount of acetic acid stoichiometrically equivalent to said chemically active calcium oxide and chemically active magnesium oxide;

d. allowing the product formed through steps a., b. and c. to freeze.

2. The process of claim 1, wherein said finely divided ore is reacted within said agitated reaction vessel with an acetic acid solution containing said measured quantity of water and said measured amount of acetic acid.

3. The process of claim 1, wherein said mol fraction of magnesium is 0.8.

4. The process of claim 1, wherein said mol fraction of magnesium is 1.0.

5. The process of claim 1, wherein the value of x equals 5.0.

6. The process of claim 5, wherein said mol fraction of magnesium is 0.8.

7. The process of claim 5, wherein said mol fraction of magnesium is 1.0.

8. The process of claim 1, wherein said product is subjected to a drying step.

9. A new composition of matter, useful as as surface deicer, having the empirical formula $$mCa(Ac)_2 \cdot n\{(Mg(Ac)_2 \cdot wH_2O\},$$

where $n/(m+n)$ is equal to 0.68–0.99, and w is equal to 3–4.

10. The composition of matter of claim 9, wherein $n/m+n$ is equal to 0.8, and w equals 3–4.

11. The process of claim 1 whereby traction agent is introduced into the reaction vessel such that fraction of traction agent, anhydrous product basis, falls in the range of 1–75%.

12. A new composition of matter, useful as a surface deicer, having the empirical formula $$mCa(Ac)_2 \cdot n(Mg(Ac)_2 \cdot wH_2O)$$

where $n/(m+n)$ equals 0.68–1.00, w equals 3–4, and incorporating within its mass 1–75% traction agent.

* * * * *